US012631642B2

(12) United States Patent
Arakawa et al.

(10) Patent No.: US 12,631,642 B2
(45) Date of Patent: May 19, 2026

(54) RENAL CANCER DETECTION METHOD AND TEST DRUG

(71) Applicants: PUBLIC UNIVERSITY CORPORATION YOKOHAMA CITY UNIVERSITY, Yokohama (JP); TOSOH CORPORATION, Shunan (JP)

(72) Inventors: Noriaki Arakawa, Yokohama (JP); Hisashi Hirano, Yokohama (JP); Noboru Nakaigawa, Yokohama (JP); Masahiro Yao, Yokohama (JP); Norihisa Ohtake, Yokohama (JP)

(73) Assignees: PUBLIC UNIVERSITY CORPORATION YOKOHAMA CITY UNIVERSITY, Kanagawa (JP); TOSOH CORPORATION, Yamaguchi (JP)

( * ) Notice: Subject to any disclaimer, the term of this patent is extended or adjusted under 35 U.S.C. 154(b) by 159 days.

(21) Appl. No.: 16/962,352

(22) PCT Filed: Dec. 26, 2018

(86) PCT No.: PCT/JP2018/047882
§ 371 (c)(1),
(2) Date: Jul. 15, 2020

(87) PCT Pub. No.: WO2019/142636
PCT Pub. Date: Jul. 25, 2019

(65) Prior Publication Data
US 2021/0063400 A1      Mar. 4, 2021

(30) Foreign Application Priority Data
Jan. 16, 2018     (JP) ................................ 2018-004737

(51) Int. Cl.
*G01N 33/574*      (2006.01)
*G01N 33/57525*      (2026.01)
*G01N 33/68*      (2006.01)

(52) U.S. Cl.
CPC ....... *G01N 33/57525* (2026.01); *G01N 33/68* (2013.01); *G01N 33/6848* (2013.01)

(58) Field of Classification Search
CPC ............. G01N 33/68; G01N 33/57438; G01N 33/6848
See application file for complete search history.

(56) References Cited

U.S. PATENT DOCUMENTS 11,193,936 B2 * 12/2021 Arakawa ................ C07K 14/47
2013/0203619 A1 * 8/2013 Copland, III ........ C12Q 1/6886
435/7.1

2014/0295456 A1    10/2014  Blonder et al.
2017/0322218 A1    11/2017  Arakawa et al.
2023/0221322 A1 *  7/2023  Shibata ............ G01N 33/57488
436/64

FOREIGN PATENT DOCUMENTS

| | | |
|---|---|---|
| CN | 107723368 A | 2/2018 |
| JP | 5224309 B2 | 7/2013 |
| JP | 6074676 B2 | 2/2017 |
| WO | 2016/084912 A1 | 6/2016 |

OTHER PUBLICATIONS

Bin Gu, Qiang Ding, Zujun Fang, Cuowei Xia, Expression and methylation status of tissue factor pathway inhibitor-2 in renal cell carcinoma, 2008, Chinese Journal of Urology, 12:12-15 (Year: 2008).*
The Human Protein Atlas, Expression of TFPI2 in Cancer, Retrieved from the Internet https://web.archive.org/web/20170826002830/http://www.proteinatlas.org/ENSG00000105825-TFPI2/pathology#gene_information: Aug. 2017,2 pages (Year: 2017).*
Vallejo, D. D., Rojas Ramirez, C., Parson, K. F., Han, Y., Gadkari, V. V., & Ruotolo, B. T., Mass Spectrometry Methods for Measuring Protein Stability, 2022, Chemical Reviews, 122(8), 7690-7719. (Year: 2022).*
Kapingidza, A.B., Kowal, K., Chruszcz, M, Antigen-Antibody Complexes, 2020, Vertebrate and Invertebrate Respiratory Proteins, Lipoproteins and other Body Fluid Proteins. Subcellular Biochemistry, vol. 94:(465-497) (Year: 2020).*
The Human Protein Atlas, TFPI2 Antibodies, Retrieved from the Internet: https://web.archive.org/web/20220826125447/https://www.proteinatlas.org/ENSG00000105825-TFP12/antibody :Aug. 2022, 2 pages (Year: 2022).*
Quintero-Ronderos, P., Arango, M. T., Castiblanco, J., Correa, N. E., & Montoya-Ortiz, G. Analysis of proteins and antibodies. (2013). El Rosario University Press. Chapter 48 (793-811) https://www.ncbi.nlm.nih.gov/books/NBK459443/ (Year: 2013).*
Almagro, J. C., & Fransson, J. (2008). Humanization of antibodies. Frontiers in bioscience : a journal and virtual library, 13, 1619-1633. (Year: 2008).*
Cook, G. (2000). Immunobiology: The Immune System in Health and Disease (4th edn) by CA Janeway, P. Travers, M. Walport and JD Capra. Immunology today, 21(4), 201 (Year: 2000).*
Edwards, B. M., Barash, S. C., Main, S. H., Choi, G. H., Minter, R., Ullrich, S., . . . & Vaughan, T. J. (2003). The remarkable flexibility of the human antibody repertoire; isolation of over one thousand different antibodies to a single protein, BLyS. Journal of molecular biology, 334(1), 103-118. (Year: 2003).*
Lloyd, C., Lowe, D., Edwards, B., Welsh, F., Dilks, T., Hardman, C., & Vaughan, T. (2009). Modelling the human immune response: performance of a 1011 human antibody repertoire against a broad panel of therapeutically relevant antigens. Protein Engineering, Design & Selection, 22(3), 159-168. (Year: 2009).*

(Continued)

*Primary Examiner* — Shafiqul Haq
(74) *Attorney, Agent, or Firm* — Sughrue Mion, PLLC

(57)      ABSTRACT

An object of the present invention is to provide a method for detecting renal cancer, and a reagent that can be used for the method. Provided is a method for detecting renal cancer, which includes measuring the amount of TFPI2 in a sample derived from a patient. An antibody that specifically recognizes NT-TFPI2 and intact TFPI2 is included in a detection reagent for renal cancer.

4 Claims, 9 Drawing Sheets
Specification includes a Sequence Listing.

(56)             References Cited

OTHER PUBLICATIONS

Brown, M., Rittenburg, M. B., Chen, C., & Roberts, V. A. (1996). Tolerance of single, but not multiple, amino acid replacements in antibody VH CDR 2: a means of minimizing B cell wastage from somatic hypermutation?. Journal of immunology (Baltimore, Md.: 1950), 156(9), 3285-3291. (Year: 1996).*

Vajdos, F. F., Adams, C. W., Breece, T. N., Presta, L. G., de Vos, A. M., & Sidhu, S. S. (2002). Comprehensive functional maps of the antigen-binding site of an anti-ErbB2 antibody obtained with shotgun scanning mutagenesis. Journal of molecular biology, 320(2), 415-428. (Year: 2002).*

Wojtukiewicz, M. Z., Sierko, E., Zimnoch, L., Kozlowski, L., & Kisiel, W. (2003). Immunohistochemical localization of tissue factor pathway inhibitor-2 in human tumor tissue. Thrombosis and haemostasis, 90(07), 140-146. (Year: 2003).*

The Human Protein Atlas, Expression of TFPI2 in Cancer, Retrieved from the Internet https://web.archive.org/web/20170826002830/http://www.proteinatlas.org/ENSG00000105825-TFPI2/pathology#gene_information: Aug. 2017,2 pages (Year: 2017) (Year: 2017).*

Arakawa, N., Kobayashi, H., Yonemoto, N., Masuishi, Y., Ino, Y., Shigetomi, H., . . . & Miyagi, E. (2016). Clinical significance of tissue factor pathway inhibitor 2, a serum biomarker candidate for ovarian clear cell carcinoma. PLoS One, 11(10), e0165609. (Year: 2016).*

Goel et al. Plasticity within the Antigen-Combining Site May Manifest as Molecular Mimicry in the Humoral Immune Response. J Immunol (2004) 173 (12): 7358-7367. (Year: 2004).*

Kapingidza et al. Antigen-Antibody Complexes. Subcellular Biochemistry, Springer Nature Switzerland AG, Gewerbestrasse, 11, 6300 Cham, Switzerland, 2020, vol. 94, pp. 465-497. (Year: 2020).*

Schmid et al. Sunitinib in the treatment of metastatic renal cell carcinoma. Therapeutic Advances in Urology, 2016, vol. 8(6) 348-371. (Year: 2016).*

Extended European Search Report dated Jul. 28, 2021 from the European Patent Office in counterpart Application No. 18901702.3.

The Human Protein Atlas, Aug. 26, 2017, Retrieved from the Internet: URL: https://www.proteinatlas.org/ENSG00000105825-TFPI2/pathology, 2 pages total.

Marek Z. Wojtukiewicz et al., "Immunohistochemical localization of tissue factor pathway inhibitor-2 in human tumor tissue", Thrombosis and Haemostasis, Cellular Proteolysis and Oncology, 2003, vol. 90, pp. 140-146 (7 pages total).

Noriaki Arakawa et al., "Secretome-Based Identification of TFPI2, A Novel Serum Biomarker for Detection of Ovarian Clear Cell Adenocarcinoma", Journal of Proteome Research, 2013, pp. 4340-4350, vol. 12.

Noriaki Arakawa et al, "Clinical Significance of Tissue Factor Pathway Inhibitor 2, a Serum Biomarker Candidate for Ovarian Clear Cell Carcinoma", PLOS ONE 11(10), 2016, pp. 1-17.

Bin Gu et al., "EGCG inhibits growth and induces apoptosis in renal cell carcinoma through TFPI-2 overexpression", Oncology Reports, Mar. 2009, pp. 635-640, vol. 21, No. 3.

Bin Gu et al. "Expression and methylation status of tissue factor pathway inhititor-2 in renal cell carcinoma", Chinese Journal of Urology, 2008, pp. 12-15.

International Search Report for PCT/JP2018/047882 mailed on Mar. 19, 2019.

Office Action issued May 9, 2023 by Japan Patent Office in Japanese Application No. 2019-566393.

Noriaki Arakawa et al., "Cell Culture-based Biomarker Discovery and Clinical Applications", Proteome Letters, 2016, vol. 1, pp. 81-87 (7 pages total).

* cited by examiner

SEQUENCE LISTING

<160> NUMBER OF SEQ ID NOS: 1

<210> SEQ ID NO 1
<211> LENGTH: 235
<212> TYPE: PRT
<213> ORGANISM: Homo Sapiens

<400> SEQUENCE: 1

```
Met Asp Pro Ala Arg Pro Leu Gly Leu Ser Ile Leu Leu Leu Phe Leu
1               5                   10                  15

Thr Glu Ala Ala Leu Gly Asp Ala Ala Gln Glu Pro Thr Gly Asn Asn
            20                  25                  30

Ala Glu Ile Cys Leu Leu Pro Leu Asp Tyr Gly Pro Cys Arg Ala Leu
        35                  40                  45

Leu Leu Arg Tyr Tyr Tyr Asp Arg Tyr Thr Gln Ser Cys Arg Gln Phe
    50                  55                  60

Leu Tyr Gly Gly Cys Glu Gly Asn Ala Asn Asn Phe Tyr Thr Trp Glu
65                  70                  75                  80

Ala Cys Asp Asp Ala Cys Trp Arg Ile Glu Lys Val Pro Lys Val Cys
                85                  90                  95

Arg Leu Gln Val Ser Val Asp Asp Gln Cys Glu Gly Ser Thr Glu Lys
                100                 105                 110

Tyr Phe Phe Asn Leu Ser Ser Met Thr Cys Glu Lys Phe Phe Ser Gly
            115                 120                 125

Gly Cys His Arg Asn Arg Ile Glu Asn Arg Phe Pro Asp Glu Ala Thr
        130                 135                 140

Cys Met Gly Phe Cys Ala Pro Lys Lys Ile Pro Ser Phe Cys Tyr Ser
145                 150                 155                 160

Pro Lys Asp Glu Gly Leu Cys Ser Ala Asn Val Thr Arg Tyr Tyr Phe
                165                 170                 175

Asn Pro Arg Tyr Arg Thr Cys Asp Ala Phe Thr Tyr Thr Gly Cys Gly
            180                 185                 190

Gly Asn Asp Asn Asn Phe Val Ser Arg Glu Asp Cys Lys Arg Ala Cys
        195                 200                 205

Ala Lys Ala Leu Lys Lys Lys Lys Met Pro Lys Leu Arg Phe Ala
    210                 215                 220

Ser Arg Ile Arg Lys Ile Arg Lys Lys Gln Phe
225                 230                 235
```

RENAL CANCER DETECTION METHOD AND TEST DRUG

CROSS-REFERENCE TO RELATED APPLICATIONS

This application is a National Stage of International Application No. PCT/JP2018/047882 filed on Dec. 26, 2018, which claims priority under U.S.C. § 119(a) to Japanese Patent Application No. 2018-004737 filed on Jan. 16, 2018, the entire contents of which are incorporated herein by reference.

TECHNICAL FIELD

The present invention relates to a method and a reagent for detecting renal cancer in which a tissue factor pathway inhibitor 2 (TFPI2) is measured.

BACKGROUND ART

The estimated morbidity of renal and urinary tract cancer excluding bladder cancer is 19.5 per 100,000 population (National Cancer Research Center Cancer Control Information Center 2013), and has been increasing in recent years. Renal cancer has few subjective symptoms and is often detected accidentally during medical examinations and physical examinations, and is considered to be a cancer that is difficult to detect early.

As a rule, renal cancer is treated by surgical resection, and as drug therapy, a molecular target drug such as a tyrosine kinase inhibitor (TKI) or an mTOR inhibitor that inhibits angiogenesis, an immune checkpoint inhibitor, and the like are used as appropriate.

Examples of blood tests for renal cancer include erythrocyte sedimentation for quantifying the erythrocyte sedimentation rate, CRP (C-reactive protein), and IAP (Immunosuppressive Acidic Protein). All of these, however, target factors arising from an inflammatory response indirectly induced by cancer, and their usefulness as tumor markers is not definitive. For this reason, ultrasonography and CT and MM imaging are currently the most effective testing methods. CT, however, involves concerns about radiation exposure, and burden on patients caused by imaging diagnosis is not low. Therefore, a simpler and less burdensome method for detecting renal cancer by blood tests is coveted.

Tissue factor pathway inhibitor 2 (TFPI2) is the same protein as placental protein 5 (PP5), and is a placenta-derived serine protease inhibitor having three Kunitz-type protease inhibitor domains. Regarding association between TFPI2 and cancer, the present inventors, Arakawa et al., elucidated that TFPI2 is specifically produced from the clear cell carcinoma cell line of ovarian cancer, and that an increased gene expression of TFPI2 in an ovarian cancer patient tissue specifically occurs only in patients with clear cell carcinoma (Patent Document 1). The inventors also discovered that blood TFPI2 is significantly increased in clear cell carcinoma relative to healthy individuals and cases of endometriosis (Patent Document 2, Non Patent Document 1). A method for detecting ovarian clear cell carcinoma by measuring TFPI2 has also been disclosed (Patent Document 3, Non Patent Document 2).

Regarding association between TFPI2 and renal cancer, it is suggested that addition of epigallocatechin gallate (ECGC) contained in green tea increases the expression level of TFPI2 in human renal cancer cell lines, suppresses cell proliferation, and induces apoptosis (Non Patent Document 3). However, to date, there have been no reports on blood kinetics of TFPI2 in renal cancer, and it was unclear whether TFPI2 can be applied to detection of renal cancer.

PRIOR ART DOCUMENTS

Patent Documents

Patent Document 1: Japanese Patent 5224309

Patent Document 2: Japanese Patent 6074676

Patent Document 3: WO2016/084912

Non Patent Documents

Non Patent Document 1: J. Proteome Res., 2013, 12 (10), pp 4340-4350

Non Patent Document 2: PloS one 11.10 (2016): e0165609.

Non Patent Document 3: Oncology reports 21.3 (2009): 635-640.

SUMMARY OF THE INVENTION

Problems to be Solved by the Invention

An object of the present invention is to provide a method for detecting renal cancer, and a reagent that can be used for the method.

Means for Solving the Problems

The present inventors intensively studied, and found that TFPI2 is secreted in culture supernatants of a plurality of renal cancer cell lines, and that blood TFPI2 is significantly increased in renal cancer patients compared with healthy individual, and arrived at an idea that TFPI2 can detect renal cancer, thereby completing the present invention.

That is, the present invention includes the following embodiments.

[1] A method for detecting renal cancer, the method comprising measuring the amount of TFPI2 in a sample.

[2] The method according to [1], wherein renal cancer is detected when the measured amount of TFPI2 exceeds a predetermined standard value.

[3] The method according to [1] or [2], wherein the amount of TFPI2 is the sum of the amount of TFPI2 processing polypeptide and the amount of intact TFPI2.

[4] The method according to any one of [1] to [3], wherein the amount of TFPI2 is measured by an antigen-antibody reaction using an antibody that binds to an antigenic determinant in the region from the 23rd residue aspartic acid to the 131st residue histidine or the 130th residue cysteine of the amino acid sequence of SEQ ID No: 1.

[5] The method according to [4], wherein the antibody is an antibody that recognizes Kunitz domain 1 of TFPI2.

[6] The method according to any one of [1] to [3], wherein measurement is carried out using mass spectrometry.

[7] A reagent for detecting renal cancer, comprising an antibody that binds to an antigenic determinant in the region from the 23th residue aspartic acid to the 131st residue histidine or to the 130th residue cysteine in the amino acid sequence of SEQ ID NO:1.

Effect of the Invention

The present invention provides a simple and highly accurate method for detecting renal cancer and a reagent that can be utilized for the method.

MODE FOR CARRYING OUT THE INVENTION

Figure 1:
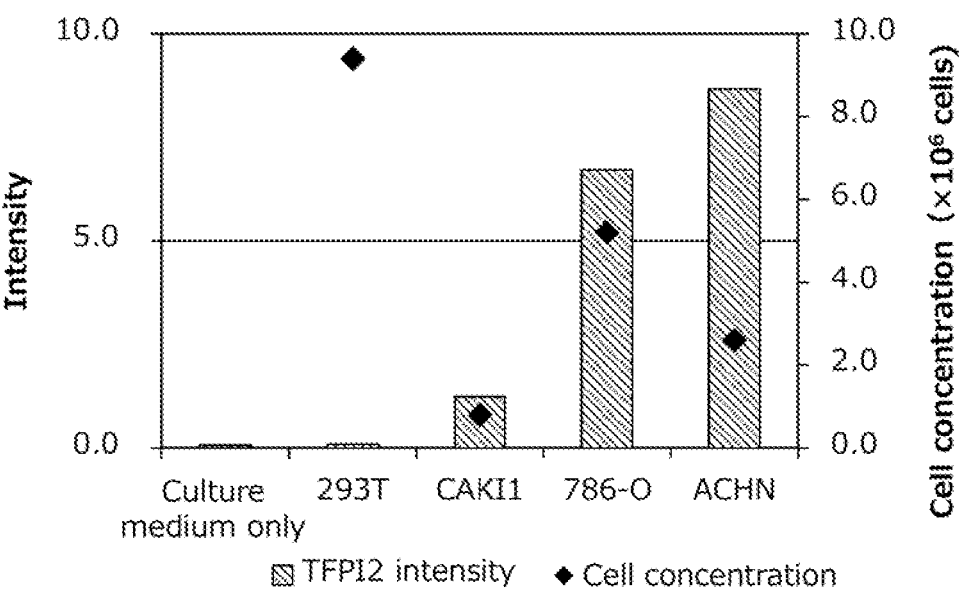
FIG. 1: The figure is a diagram showing the amount of TFPI2 in cell line culture supernatant. The first ordinate represents a TFPI2 measurement value, and the second ordinate represents the number of cells.

<1> Method for Detecting Renal Cancer of Present Invention

A first aspect of the present invention is a method for detecting renal cancer, which includes measuring the amount of TFPI2 in a sample. This is a method based on the fact that TFPI2 is characteristically present in a biological sample such as blood of renal cancer as compared with a healthy sample. The measurement of the amount of TFPI2 in a sample is usually performed in vitro. By this method, renal cancer can be detected with high sensitivity and specificity, as shown in Examples described below.

The method of the present invention includes up to a step of detecting renal cancer, and does not include the final act of determining the diagnosis of renal cancer. A doctor diagnoses renal cancer or makes a treatment policy by referring to a detection result and the like by the method of the present invention.

TFPI2 measured in the present invention is not particularly limited, and may be, for example, intact TFPI2 (hereinafter, also referred to as "I-TFPI2") and/or TFPI2 processing polypeptide (hereinafter, also referred to as "NT-TFPI2").

SEQ ID NO:1 shows an amino acid sequence based on the human TFPI2 cDNA. In SEQ ID NO:1, a signal peptide extends from the initiation methionine to the 22nd residue glycine.

"Intact TFPI2" means the peptide represented by the 23rd to 235th residues in the amino acid sequence of SEQ ID NO:1.

"NT-TFPI2" means a peptide fragment containing a Kunitz domain 1 located on the N-terminal side of intact TFPI2, as described in Patent Document 3. More specifically, NT-TFPI2 is a peptide containing at least a sequence from the 23rd residue aspartic acid to the 131st residue histidine or the 130th residue cysteine of the amino acid sequence of SEQ ID NO:1 or a peptide containing an amino acid sequence having 80% or more identity with the above-described sequence. The identity is preferably not less than 90%, more preferably not less than 95%. The polypeptide of the present invention may be a polypeptide having a sequence which is the same as the above sequence except that one or several amino acids are deleted, substituted, inserted, and/or added. The term "several" means preferably 2 to 20, more preferably 2 to 10, still more preferably 2 to 5. Although NT-TFPI2 may also have other peptide fragments in both sides of the above sequence, it preferably does not have an antigenic determinant for an antibody that recognizes Kunitz domain 3 of TFPI2.

Examples of the patient-derived sample (test sample) in the present invention include blood components such as whole blood, blood cells, serum, and plasma, cell or tissue extract, urine, and cerebrospinal fluid. A renal tissue biopsy sample may be used as a test target, and in that case, an extract of the biopsy sample or a culture supernatant is measured. It is preferable to use a body fluid such as a blood component or urine as a sample because a test can be performed easily and non-invasively, and considering the ease of collecting a sample and the versatility of other test items, it is particularly preferable to use a blood component as a sample. The sample dilution ratio may be appropriately selected from undiluted to 100-fold diluted according to the type and state of a sample to be used.

The sampling time of the sample in the present invention is not particularly limited. For example, a sample can be collected at any time from a preoperative period when renal cancer is suspected due to image diagnosis or the like and detailed examination is performed to a follow-up period after definitive diagnosis of renal cancer by postoperative pathological examination, and any sample collected at any stage such as before and after definitive diagnosis and before and after the start of treatment can be used in the method of the present invention.

In the detection method of the present invention, it is preferable to determine that renal cancer is detected when the amount of TFPI2 obtained by the measurement exceeds a preset standard value (Cutoff value). Here, the TFPI2 amount may be either an intact TFPI2 amount, an NT-TFPI2 amount, or a total of an intact TFPI2 amount and an NT-TFPI2 amount, and the total of the intact TFPI2 amount and the NT-TFPI2 amount is more preferable from the viewpoint of achieving both easy measurement and sufficient sensitivity and specificity.

The standard value used for the determination may be either the measured value or the converted concentration value. The converted concentration value means a value converted from the measured value based on a calibration curve prepared using TFPI2 as a standard sample.

The standard value (Cutoff value) for determining renal cancer can be appropriately set to a measured value showing optimum sensitivity and specificity by measuring healthy individuals and renal cancers and analyzing receiver operating characteristic (ROC) curve. For example, the standard value of TFPI2 may be set to 219 pg/mL in the case of plasma and 189 pg/mL or 200 pg/mL in the case of serum, as described in the Examples below, but is not limited thereto.

Hereinafter, a method for measuring TFPI2 will be described.

In the present invention, the amount of NT-TFPI2 or the amount of intact TFPI2 in a sample may be individually measured, or the values may be summed to obtain the total amount. The total amount of NT-TFPI2 and intact TFPI2 in a sample may be measured with a measurement system capable of measuring at one time. Alternatively, as described later, the amount of NT-TFPI2 may be indirectly measured from the total amount of both measurements and the measured amount of intact TFPI2 alone.

In the method of the present invention, the method for measuring the amount of NT-TFPI2 and/or the amount of intact TFPI2 is not limited. Examples of the method include methods utilizing antigen-antibody reaction in which an antibody that recognizes NT-TFPI2 and/or intact TFPI2 is used, and methods utilizing mass spectrometry.

(a) A competition method using a labeled measuring object and an antibody that recognizes the measuring object, which method utilizes competitive binding of the labeled measuring object and the measuring object contained in the sample to the antibody.

(b) A method using surface plasmon resonance, wherein the sample is brought into contact with a chip on which an antibody that recognizes the measuring object is immobilized, and a signal dependent on binding of the antibody to the measuring object is detected.

(c) A fluorescence polarization immunoassay using a fluorescently labeled antibody that recognizes a measuring object, which immunoassay utilizes the phenomenon that binding of the antibody to the measuring object causes an increase in the degree of fluorescence polarization.

(d) A sandwich method using two kinds of antibodies (one of which is a labeled antibody) that recognize the measuring object at different epitopes, wherein formation of a complex of the three molecules, that is, the two antibodies and the measuring object, is allowed to occur.

(e) A method in which pretreatment is carried out by concentrating the measuring object in the sample using an antibody that recognizes the measuring object, and the polypeptide in the bound protein is detected using a mass spectrometer or the like.

Although the methods (d) and (e) are simple and versatile, the method (d) is preferable for processing of a large number of samples since the technologies related to the reagents and the devices for this method have been sufficiently established.

Specific examples of the methods for measuring the amount of NT-TFPI2 and/or the amount of intact TFPI2 utilizing antigen-antibody reaction include the following.

(A) A method using an antibody that recognizes both NT-TFPI2 and intact TFPI2, wherein the total amount of NT-TFPI2 and intact TFPI2 is measured (NT+I-TFPI2 assay system). The antibody that recognizes both NT-TFPI2 and intact TFPI2 is preferably an antibody that binds to an antigenic determinant in the region from the 23th residue aspartic acid to the 131st residue histidine or to the 130th residue cysteine in the TFPI2 amino acid sequence represented by SEQ ID NO:1. The antibody is more preferably an antibody having an antigenic determinant in Kunitz domain 1 of TFPI2. In cases where the above-mentioned sandwich method is used in this method, two kinds of antibodies for different epitopes are used as the antibody.

(B) A method using an antibody that does not recognize NT-TFPI2 but recognizes intact TFPI2, wherein the amount intact TFPI2 alone is measured (I-TFPI2 assay system). The antibody that does not recognize NT-TFPI2 but recognizes intact TFPI2 is preferably an antibody having an antigenic determinant in Kunitz domain 3 of TFPI2. In cases where the above-mentioned sandwich method is used in this method, two kinds of antibodies for different epitopes are used as the antibody. At least one of these is an antibody that does not recognize NT-TFPI2 but recognizes intact TFPI2, and the other may be either an antibody that does not recognize NT-TFPI2 but recognizes intact TFPI2, or an antibody that recognizes both NT-TFPI2 and intact TFPI2.

(C) A method in which the amount of intact TFPI2 alone measured in the I-TFPI2 assay system of (B) is subtracted from the total amount of NT-TFPI2 and intact TFPI2 measured in the NT+I-TFPI2 assay system of (A), to calculate the amount of NT-TFPI2 alone.

(D) A method using an antibody that does not recognize intact TFPI2 but recognizes NT-TFPI2, wherein the amount NT-TFPI2 alone is measured. Examples of the antibody that does not recognize intact TFPI2 but recognizes NT-TFPI2 include antibodies that specifically recognize a peptide sequence in the C-terminal portion of NT-TFPI2. For example, in cases where the above-mentioned sandwich method is used, such an antibody is used as the solid-phase antibody, and an antibody having a recognition site in Kunitz domain 1 is used as the detection antibody.

In the method for detecting renal cancer of the present invention, the amount of NT-TFPI2 alone measured by the method of (C) or (D) may be used as a criterion. However, sufficient sensitivity and specificity can be obtained also by using the total amount of NT-TFPI2 and intact TFPI2 measured by the method of (A) as a criterion. The latter method is preferable from the viewpoint of the fact that the antibody can be easily obtained, and that the measurement can be simply carried out by a single step.

An antibody that recognizes NT-TFPI2 and/or intact TFPI2 can be obtained by immunizing an animal using as an immunogen, for example, an NT-TFPI2 polypeptide or protein, an oligopeptide composed of a partial region of the intact TFPI2 polypeptide or the TFPI2 protein, or a polynucleotide encoding the intact or a partial region of the NT-TFPI2 polypeptide or of the TFPI2 protein. The protein or the oligopeptide or polypeptide may not reflect the three-dimensional structure of TFPI2 in a living body, or the structure thereof may change during a preparation process. Therefore, an obtained antibody may not have high specificity or binding capacity to TFPI2 in a desired living body, and even when a measurement system is constructed using the present antibody, the TFPI2 concentration contained in a sample as a result may not be accurately quantified.

On the other hand, when an expression vector containing a polynucleotide encoding an intact or partial region of a TFPI2 polypeptide or an intact TFPI2 protein is used as an immunogen, the intact or partial region of the TFPI2 polypeptide or intact TFPI2 protein is expressed in an immunized animal, an immune response is elicited, and an antibody having high specificity and binding capacity (that is, high affinity) to the TFPI2 in a sample is obtained, which is preferable.

The animal to be used for the immunization is not limited as long as the animal has ability to produce antibodies. The animal may be a mammal normally used for immunization, such as a mouse, a rat, or a rabbit, or may be a bird such as a chicken.

In blood, there is also TFPI1, known as a homologue of TFPI2. Therefore, it is desirable to use an antibody that does not cross with TFPI1 but specifically recognizes only TFPI2.

Another aspect of the present invention is use of a reagent for measuring the amount of TFPI2 in manufacturing of a reagent for detecting renal cancer. Here, the reagent for measuring the amount of TFPI2 is preferably a reagent for measuring the total of the amount of TFPI2 processing polypeptide and the amount of intact TFPI2. The reagent for measuring the amount of TFPI2 is preferably an antibody that binds to an antigenic determinant in a region from the 23rd residue aspartic acid to the 131st residue histidine or the 130th residue cysteine of the amino acid sequence of SEQ ID NO:1, and more preferably an antibody that recognizes Kunitz domain 1 of TFPI2.

Therefore, the present invention can be also said to be use of an antibody that binds to an antigenic determinant in a region from the 23rd residue aspartic acid to the 131st residue histidine or the 130th residue cysteine of the amino acid sequence of SEQ ID NO:1 in manufacturing of a reagent for detecting renal cancer.

The present invention can also be said to be the use of an antibody that binds to an antigenic determinant in a region from the 23rd residue aspartic acid to the 131st residue histidine or the 130th residue cysteine of the amino acid sequence of SEQ ID NO:1 in the detection of renal cancer.

The antibody that recognizes TFPI2 may be either a monoclonal antibody or a polyclonal antibody. The antibody is preferably a monoclonal antibody.

The method of establishment of a hybridoma cell that produces an antibody that recognizes TFPI2 may be appropriately selected from methods whose techniques have been established. For example, a hybridoma cell that produces a monoclonal antibody that recognizes TFPI2 can be established by collecting B cells from an animal immunized by the above method, fusing the B cells with myeloma cells electrically or in the presence of polyethylene glycol, selecting a hybridoma cell that produces a desired antibody using HAT medium, and preparing the selected hybridoma cell into a monoclone by the limiting dilution method.

The selection of the monoclonal antibody that recognizes TFPI2 used in the present invention may be carried out based on affinity to GPI (glycosylphosphatidylinositol)-anchor type TFPI2 or secretory TFPI2 derived from a host expression system.

The host is not limited, and may be appropriately selected from microorganisms such as *E. coli* or yeast, insect cells, and animal cells that are usually used for protein expression by those skilled in the art. The host is preferably a mammalian cell since it enables expression of a protein having a structure similar to that of natural TFPI2 by post-translational modification such as disulfide bonding or glycosylation. Examples of the mammalian cell include the human embryonic kidney (HEK)-derived 293T cell line, monkey kidney COS7 cell line, Chinese hamster ovary (CHO) cells, and cancer cells isolated from human.

The method of purification of the antibody to be used in present invention may be appropriately selected from methods whose techniques have been established. For example, after culturing hybridoma cells which are established by the above method and which produce an antibody, the culture supernatant may be collected, and the antibody may be concentrated, if necessary, by ammonium sulfate precipitation. Thereafter, by affinity chromatography using a carrier to which Protein A, Protein G, Protein L, or the like is immobilized, and/or by ion-exchange chromatography, purification of the antibody is possible.

The labeled antibody used for the antigen-antibody reaction in the sandwich method described above may be prepared by labeling an antibody purified by the above method with an enzyme such as peroxidase or alkaline phosphatase. The labeling may also be carried out using a method whose technique has been sufficiently established.

The method for measuring the amount of TFPI2 utilizing mass spectrometry in the method of the present invention is described below concretely.

In cases of a blood sample, a pretreatment step is preferably carried out by removing major proteins contained in large amounts in blood such as albumin, immunoglobulin, and transferrin using Agilent Human 14 or the like, and performing further fractionation by ion exchange, gel filtration, reverse-phase HPLC, and/or the like. Alternatively, only TFPI2 can be specifically recovered by an immunological method using an anti-TFPI2 antibody.

The measurement can be carried out by tandem mass spectrometry (MS/MS), liquid chromatography-tandem mass spectrometry (LC/MS/MS), matrix assisted laser desorption ionization time-of-flight mass spectrometry (MALDI-TOF/MS), surface enhanced laser desorption ionization mass spectrometry (SELDI-MS), or the like.

<2> Reagent for Detecting Renal Cancer of Present Invention

In cases where the reagent of the present invention is used in the sandwich method described above, the reagent preferably contains, as the antibody, two kinds of antibodies for different epitopes.

The antibody contained in the reagent of the present invention may be an antibody itself, a labeled antibody, or an antibody immobilized on a solid phase.

The reagent of the present invention is described below concretely for cases where it is used for a two-step sandwich method, which is one mode of the sandwich method. However, the present invention is not limited thereto.

The reagent of the present invention can be prepared by the method described in the following (I) to (III).

(I) First, Antibody 1, one of the two kinds of antibodies for different epitopes that recognize TFPI2 (hereinafter referred to as "Antibody 1" and "Antibody 2"), is bound to a carrier capable of B/F (Bound/Free) separation such as an immunoplate or magnetic particles. The binding method may be either physical binding utilizing hydrophobic bonding, or chemical bonding using a linker reagent capable of cross-linking two substances to each other.

(II) After the binding of the Antibody 1 to the carrier, the carrier surface is subjected to blocking treatment using bovine serum albumin, skim milk, a commercially available immunoassay blocking agent, or the like for preventing non-specific binding, to provide a primary reagent.

(III) After labeling the other antibody, Antibody 2, a solution containing the obtained labeled antibody is provided as a secondary reagent. Preferred examples of the substance with which Antibody 2 is labeled include enzymes such as peroxidase and alkaline phosphatase; substances detectable with detection devices, such as fluorescent substances, chemiluminescent substances, and radioisotopes; and substances to which another molecule specifically binds, such as biotin, to which avidin specifically binds. Preferred examples of the solution for the secondary reagent include buffers with which antigen-antibody reaction can be favorably carried out, such as phosphate buffer and Tris-HCl buffer. The thus prepared reagent of the present invention may be freeze-dried, if necessary.

In cases of a one-step sandwich method, binding of Antibody 1 to the carrier and subsequent blocking treatment may be carried out in the same manner as in (I) and (II) to prepare an antibody-immobilized carrier, and a buffer containing a labeled Antibody 2 may be further added to the antibody-immobilized carrier, to provide a reagent.

For measurement of TFPI2 by a two-step sandwich method using reagents obtained by the method described above, the method described in the following (IV) to (VI) may be carried out.

(IV) The primary reagent prepared in (II) is brought into contact with a sample for a predetermined period of time at a constant temperature. In terms of the reaction conditions, the reaction may be carried out at a temperature within the range of 4° C. to 40° C. for 5 minutes to 180 minutes.

(V) Unreacted substances are removed by B/F separation, and then the secondary reagent prepared in (III) is brought into contact with the resulting reaction product for a predetermined period of time at a constant temperature to allow formation of a sandwich complex. In terms of the reaction conditions, the reaction may be carried out at a temperature within the range of 4° C. to 40° C. for 5 minutes to 180 minutes.

(VI) Unreacted substances are removed by B/F separation, and the labeling substance of the labeled antibody is quantified. Based on a calibration curve prepared using a TFPI2 solution having a known concentration as a standard sample, the human TFPI2 in the sample is quantified.

The amount of each reagent component such as the antibody contained in the agent may be appropriately set depending on conditions such as the amount of the sample, the type of the sample, the type of the reagent, and the measurement method. More specifically, for example, in cases where the amount of TFPI2 are measured as described below by a sandwich method using 20 μL of serum or plasma as a sample, the amount of the antibody to be bound to the carrier may be 100 ng to 1000 μg, and the amount of the labeled antibody may be 2 ng to 20 μg per the reaction system in which 20 μL of the sample is reacted with the antibodies.

The reagent of the present invention is applicable to either manual measurement or measurement using an automatic immunodiagnostic device. Measurement using an automatic immunodiagnostic device is especially preferable since it enables the measurement without being influenced by endogenous measurement-inhibiting factors and competing enzymes contained in the sample, and also enables rapid quantification of the concentration of TFPI2.

The method for detecting renal cancer of the present invention can be applied to the method for treating renal cancer.

That is, according to the present invention, provided is a method for treating renal cancer in a test subject, including:

(i) a step in which a test subject is identified as one in which a measured value of the TFPI2 amount exceeds a preset standard value;

(ii) a step in which a treatment is provided to the test subject identified as having a measured amount of TFPI2 above a preset standard value.

In a preferred aspect of the method for treating renal cancer, the amount of TFPI2 is the sum of the amount of TFPI2 processing polypeptide and the amount of intact TFPI2.

In the identification of the step (i), the amount of TFPI2 is preferably measured by an antigen-antibody reaction using an antibody that binds to an antigenic determinant in the region from the 23rd residue aspartic acid to the 131st residue histidine or the 130th residue cysteine of the amino acid sequence of SEQ ID No: 1. More preferably, the antibody is an antibody that recognizes Kunitz domain 1 of TFPI2.

In the identification of the step (i), the measurement of the amount of TFPI2 may be performed by mass spectrometry.

Examples of the treatment of the step (ii) include surgical resection, drug therapy, and radiation therapy, and examples of the drug include tyrosine kinase inhibitors, mTOR inhibitors, and immune checkpoint inhibitors, but are not particularly limited.

EXAMPLES

Examples are shown below for concrete description of the present invention. However, these Examples merely show examples of the present invention, and the present invention is not limited by Examples.

<Example 1> Preparation of Reagent for TFPI2 Measurement

According to the method of Patent Document 3, a reagent for TFPI2 measurement was prepared using a TFPI2 antibody obtained by the DNA immunization method as follows.

(1) Physical adsorption of an anti-TFPI2 monoclonal antibody (TS-TF04) to water-insoluble ferrite carriers was allowed at room temperature for one day and night such that the adsorption occurred at 100 ng/carrier, and blocking was then carried out with 100 mM Tris buffer (pH 8.0) supplemented with 1% BSA at 53° C. for 4 hours, to prepare anti-TFPI2 antibody-immobilized carriers.

(2) An alkaline phosphatase labeled anti-TFPI2 antibody was prepared with anti-TFPI2 monoclonal antibodies (TS-TF01) using an alkaline phosphatase labeling kit (manufactured by Dojindo Laboratories).

(3) In each of magnetic force-permeable containers (volume, 1.2 mL), 12 antibody-immobilized carriers prepared in (1) were placed, and 100 μL of a buffer (Tris buffer supplemented with 3% BSA, pH 8.0) supplemented with 1 μg/mL of an alkaline phosphatase labeled antibody prepared in (2) was added thereto, followed by carrying out freeze-drying, to prepare a TFPI2 assay reagent. The TFPI2 assay reagents prepared were tightly closed and sealed under nitrogen gas, and stored at 4° C. until the assay.

<Example 2> Evaluation of Cell Culture Supernatants Including Renal Cancer

293 T cells from human fetal kidney as normal cells, and CAKI1, ACHN, and 786-0 cells as renal cancer cells were cultured at 37° C. for 3 days according to a conventional method, and the number of cells was measured after collecting various culture supernatants. The culture medium alone and 20 μL of culture supernatants were evaluated with the reagent for measuring TFPI2 prepared in Example 1. As an evaluation device, a fully automatic enzyme immunoassay device AIA-2000 (manufactured by Tosoh Corporation;

manufacturing/marketing notification number, 13B3X90002000009) was used. The measurement of TFPI2 by the fully automatic enzyme immunoassay device AIA-2000 was carried out by the following procedure.

(1) By automatically dispensing 20 μL of a sample and 80 μL of a diluent containing a surfactant to a container storing a TFPI2 assay reagent prepared in Example 1;

(2) carrying out antigen-antibody reaction at a constant temperature of 37° C. for 10 minutes;

(3) carrying out eight times of washing using a buffer containing a surfactant after B/F separation; and (4) adding 4-methylumbelliferyl phosphate to the container, the concentration of 4-methylumbelliferone produced by alkaline phosphatase per unit time was provided as the measured value (TFPI2 intensity, nmol/(L·s)).

The evaluation result is shown in FIG. 1. TFPI2 clearly showed a high value in the culture supernatants of the three types of renal cancer cells as compared with 293T cells, and it was revealed that renal cancer cells secreted TFPI2 in the culture supernatants.

<Example 3> Evaluation of Clinical Samples

The clinical samples used in the following Examples are shown in Table 1. Twenty-one cases of renal cancer plasma were collected by the Yokohama City University Urology Department under the same protocol, which were provided with informed consent and the approval of the Yokohama City University Ethics Committee. Forty-nine cases of plasma of healthy individuals were purchased from Biz-ComJapan, Inc.

Clinical samples were measured by the method described in Example 2, a calibration curve was prepared using a commercially available TFPI2 recombinant protein (Tech-noPro, Inc. TechnoPro R&D, Company) as a standard, and the TFPI2 concentration in the sample was calculated.

TABLE 1

|  | Number of cases | Median age (standard deviation) |
|---|---|---|
| Healthy | 49 | 58 (±3) |
| Renal cancer | 21 | 65 (±11) |
|  | 70 |  |

Figure 2:
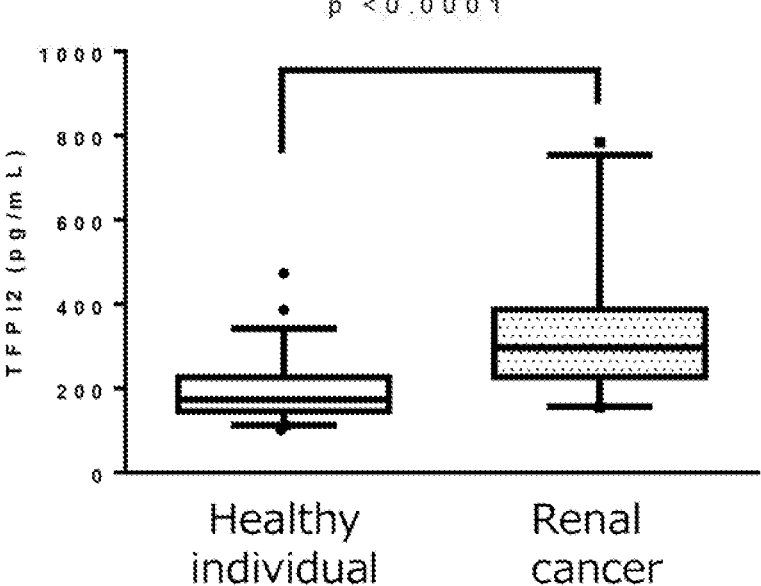
FIG. 2: The figure is a diagram showing TFPI2 measurement values in a healthy individual group and a renal cancer patient group in box plot. The ordinate represents the amount of TFPI2 in blood.

BoxPlot of the TFPI2 measurement result is shown in FIG. 2. It was revealed that TFPI2 showed a high value with a statistically significant difference in renal cancer as compared with healthy individuals (Mann-Whitney U test, p<0.0001).

Figure 3:
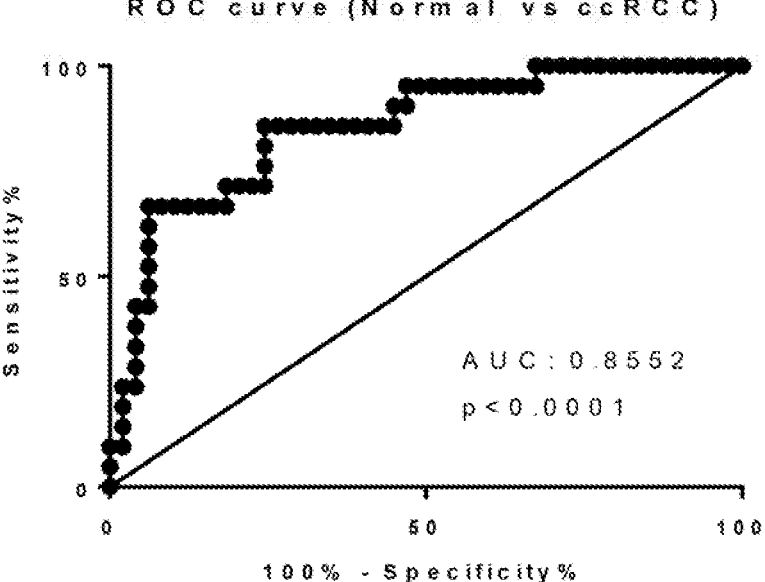
FIG. 3: The figure is a diagram showing a receiver operating characteristic (ROC) curve of a healthy individual group and a renal cancer group. The ordinate represents the sensitivity and the abscissa represents the 100%-specificity.

The ROC analysis result is shown in FIG. 3. The area under the curve (AUC) was 0.8552, indicating that TFPI2 had favorable renal cancer detection performance. The Youden Index maximum value was set as the TFPI2 cutoff value based on the Youden Index ((sensitivity+specificity)−100). When the cutoff value of TFPI2 was set to 219 pg/mL, the sensitivity was 85.7% and the specificity was 75.5%, showing that the renal cancer detection performance was favorable.

<Example 4> Association Between Histological Grade and TFPI2

Figure 4:
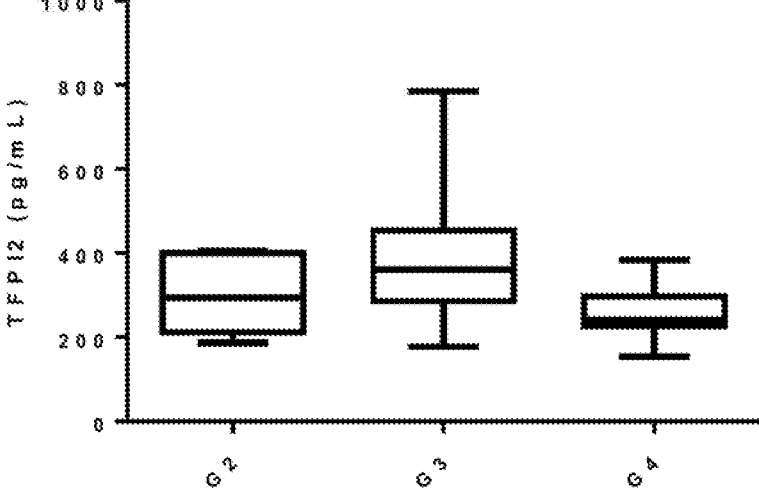
FIG. 4: The figure is a diagram showing TFPI2 measurement values in renal cancer groups classified by histological grade in box plot. The ordinate represents the TFPI2 measurement value.

The renal cancer specimen groups were classified by histological grade (grade: G), and the BoxPlot of the TFPI2 measurement value of each group is shown in FIG. 4. TFPI2 was not significantly different between the low grade 2 and the high grades 3 and 4. These results suggest that TFPI2 was not associated with histological grade and that TFPI2 expression was improved even in the early stage of renal cancer.

<Example 5> Correlation Analysis of Tumor Diameter and TFPI2

Figure 5:
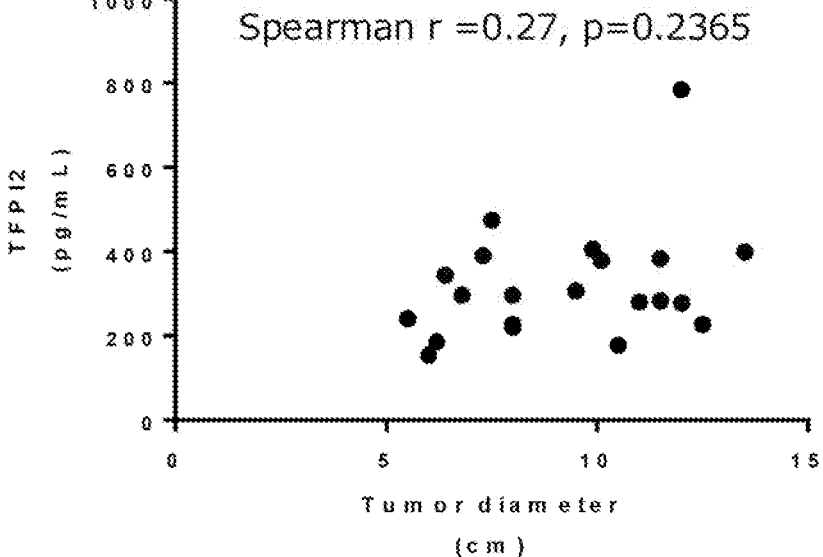
FIG. 5: The figure is a diagram showing correlation between the renal cancer tumor diameter and the TFPI2 measurement value. The ordinate represents the TFPI2 measurement value, and the abscissa represents the tumor diameter.

The result of analysis of the correlation between renal cancer tumor diameter and TFPI2 is shown in FIG. 5. There was a low positive correlation between TFPI2 and tumor diameter, but no statistically significant difference (Spearman rank correlation coefficient, r=0.27, p=0.2365).

<Example 6> Association Between Cancer Metastasis and TFPI2

Figure 6:
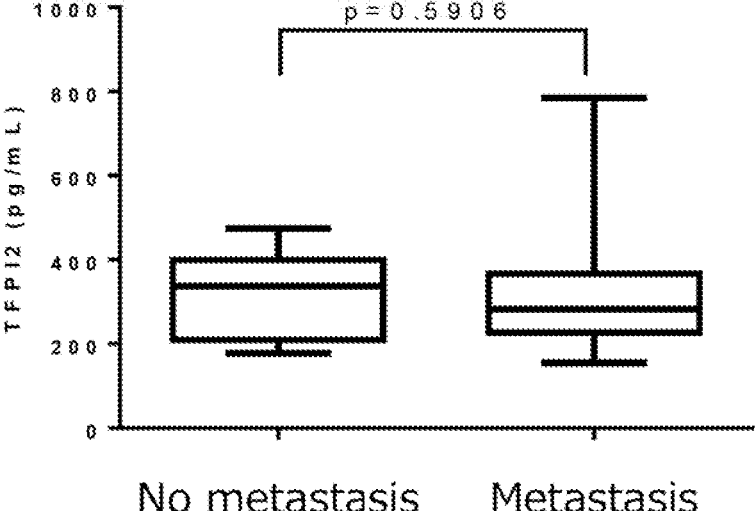
FIG. 6: The figure is a diagram showing TFPI2 measurement values in a renal cancer group classified by the presence or absence of metastasis in box plot. The ordinate represents the TFPI2 measurement value.

The renal cancer sample group was classified into two groups depending on the presence or absence of metastasis, and BoxPlot of TFPI2 measurement values of each group is shown in FIG. 6. No statistically significant difference was observed in the TFPI2 measurement values between the two groups (Mann-Whitney U test, p=0.5906), and there was no clear relationship between TFPI2 and metastasis.

<Example 7> Calculation of TFPI2 Standard Value and Reference Interval in Healthy Japanese Subjects 102 sera of healthy male subjects were in-house volunteer samples collected with informed consent, and 120 sera of healthy female subjects were provided at Yokohama City University with informed consent and the approval of the Yokohama City University Ethics Committee. TFPI2 was measured by the method described in Example 3, and a standard value range for healthy individuals was calculated according to the standard value for TFPI2 in healthy individuals (for example, median value+2SD) and CLSI guideline EP28-A3.

Figure 7:
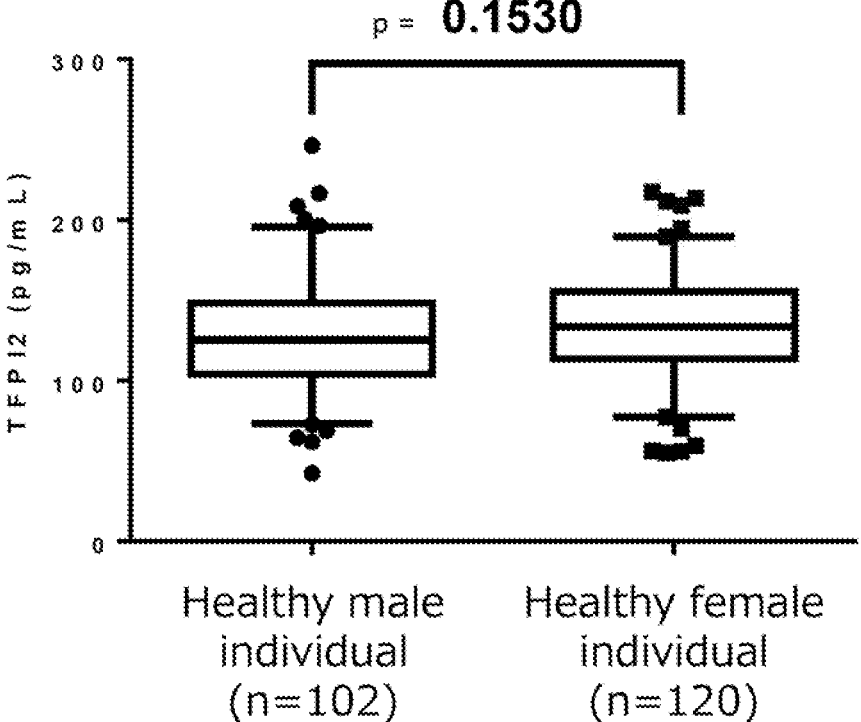
FIG. 7: The figure is a diagram showing TFPI2 measurement values in Example 7 in box plot.

The BoxPlot of the TFPI2 measurement result is shown in FIG. 7, and the standard value and reference interval calculated from healthy individuals are shown in Table 2. As a result of this study, there was no gender difference in TFPI2 measurement values in Japanese healthy individuals, and the standard value of TFPI2 calculated from the median+2SD of healthy individuals was 200 pg/mL.

TABLE 2

|  | TFPI2 (pg/mL) | | |
|---|---|---|---|
|  | Male | Female | Male + Female |
| Minimum value | 43 | 55 | 43 |
| 25% percentile | 104 | 107 | 109 |
| Median | 125 | 132 | 131 |
| 75% percentile | 148 | 156 | 151 |
| Maximum value | 246 | 223 | 246 |
| 95% confidence interval | 127-139 | 126-123 | 126-136 |
| Standard value (median + 2SD) | 197 | 198 | 200 |
| Reference interval | 63-212 | 56-211 | 61-210 |

<Example 8> Evaluation of Clinical Samples 52 cases of renal cancer serum (clear cell carcinoma: 40 cases, papillary carcinoma: 4 cases, other renal cancer: 8 cases) were specimens collected by the same protocol at Yokohama City University Urology Department, and were provided with informed consent and the approval of the Yokohama City University Ethics Committee.

TFPI2 was measured by the method described in Example 3, and the renal cancer detection performance was evaluated using the TFPI2 measurement value of a healthy individual described in Example 7.

Figure 8:
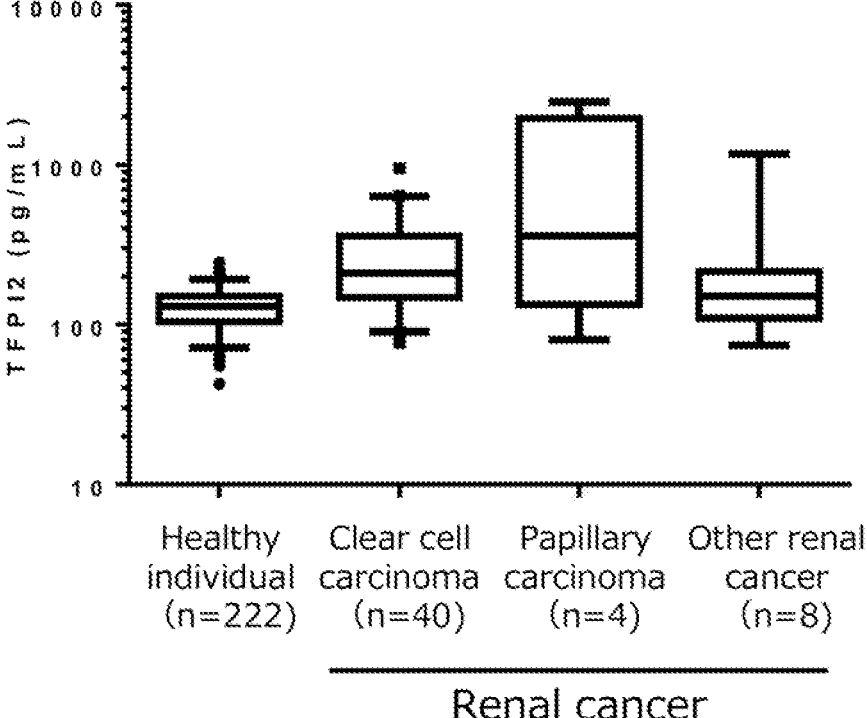
FIG. 8: The figure is a diagram showing TFPI2 measurement values in Example 8 in box plot.

FIG. 8 shows the TFPI2 measurement value in BoxPlot. TFPI2 tended to have a high value in clear cell carcinoma and papillary carcinoma in the histological type of renal cancer, and also showed a high value in some of the histological types classified into other types.

Figure 9:
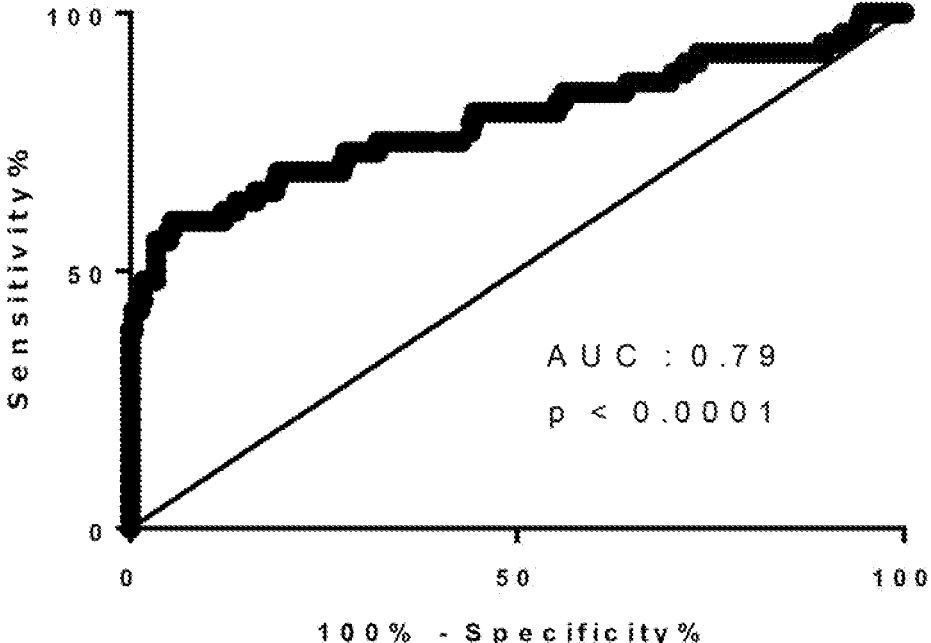
FIG. 9: The figure is a diagram showing the results of ROC curve analysis for discriminating between healthy individuals and renal cancer patients in Example 8.

FIG. 9 is an ROC curve analysis result when healthy individuals and renal cancer patients were compared. The area under the curve (AUC) was 0.79, indicating that TFPI2 had favorable renal cancer detection performance. When a Youden Index maximum value of 189 pg/mL was used as a standard value based on Youden Index ((sensitivity+specificity)−100), the discrimination performance between renal cancer patients and healthy individuals was a sensitivity of 59.6% and a specificity of 94.6%.

From the above results, it was shown that TFPI2 had favorable renal cancer detection performance by setting a suitable standard value in serum, as in plasma described in Example 3.

INDUSTRIAL APPLICABILITY

The present invention provides a method for detecting a renal cancer patient by a blood test that is simple and has a relatively low burden on the patient. This is expected to contribute to medical treatment of renal cancer, which does not have an effective tumor marker and depends on image diagnosis, and is industrially considerably useful.

---

The invention claimed is:

1. A method of detecting and treating renal cancer in a subject, said method comprising:

measuring the amount of tissue factor pathway inhibitor 2 (TFPI2) in a sample from the subject, detecting the subject having renal cancer when said measured amount of TFPI2 exceeds a predetermined standard value, and treating the subject detected with the renal cancer with a method for the treatment of the renal cancer selected from the group consisting of surgical resection, drug therapy, and radiation therapy, wherein the subject is a subject with suspected renal cancer or a subject under follow-up after definitive diagnosis of renal cancer, wherein the standard value is a measured value showing optimum sensitivity and specificity by measuring healthy individuals and renal cancers and analyzing receiver operating characteristic (ROC) curve, wherein the sample is serum or plasma, and the drug for the drug therapy is selected from the group consisting of tyrosine kinase inhibitors, mTOR inhibitors, and immune checkpoint inhibitors.

2. The method according to claim 1, wherein said amount of TFPI2 is the sum of the amount of TFPI2 processing polypeptide and the amount of intact TFPI2.

3. The method according to claim 1, wherein measurement is carried out using mass spectrometry.

4. The method according to claim 1, wherein the standard value is 219 pg/mL in the case of plasma and 189 pg/mL or 200 pg/mL in the case of serum.

\* \* \* \* \*